(12) United States Patent
Akers et al.

(10) Patent No.: US 6,178,218 B1
(45) Date of Patent: Jan. 23, 2001

(54) NONDESTRUCTIVE EXAMINATION USING NEUTRON ACTIVATED POSITRON ANNIHILATION

(75) Inventors: Douglas W. Akers; Arthur B. Denison, both of Idaho Falls, ID (US)

(73) Assignee: Bechtel BWXT Idaho, LLC, Idaho Falls, ID (US)

( * ) Notice: Under 35 U.S.C. 154(b), the term of this patent shall be extended for 0 days.

(21) Appl. No.: 09/314,602

(22) Filed: May 19, 1999

Related U.S. Application Data

(63) Continuation-in-part of application No. 08/552,349, filed on Nov. 2, 1995, now abandoned.

(51) Int. Cl.⁷ .................................................. G21G 1/00
(52) U.S. Cl. ......................... 376/159; 376/245; 250/307; 250/358.1; 250/363.03
(58) Field of Search .................... 376/159, 157, 376/245; 250/358.1, 390.04, 390.05, 306, 307, 370.1, 362, 363.03, 363.04

(56) References Cited

U.S. PATENT DOCUMENTS

| | | | |
|---|---|---|---|
| 2,509,344 | * 5/1950 | Herzog | 376/159 |
| 2,811,650 | * 10/1957 | Wagner | 376/159 |
| 3,593,025 | * 7/1971 | Grosskreutz | 250/358.1 |
| 3,792,253 | * 2/1974 | Wylie et al. | 250/83.3 R |
| 3,924,125 | * 12/1975 | Murray | 250/303 |
| 4,064,438 | * 12/1977 | Alex et al. | 250/358.1 |
| 4,463,263 | * 7/1984 | Padawer | 250/358.1 |
| 4,622,200 | * 11/1986 | Gold et al. | 376/159 |
| 4,897,549 | * 1/1990 | Zerda et al. | 250/358.1 |
| 4,983,841 | * 1/1991 | Stewart et al. | 250/358.1 |
| 5,200,619 | 4/1993 | Kumar et al. | 250/307 |
| 5,530,245 | * 6/1996 | Huang | 250/307 |

OTHER PUBLICATIONS

*Positron Annihilation*, North–Holland Pub. Co., pp. 877–879, McGervey et al., 1982.*
*Positron Annihilation*, North–Holland Pub. Co., pp. 871–873, Coleman et al, 1982.*
Nuc. Tech., vol. 104, No. 1, pp. 52–63, Pareja et al, Oct. 1993.*

* cited by examiner

Primary Examiner—Harvey E. Behrend
(74) Attorney, Agent, or Firm—Alan D. Kirsch

(57) ABSTRACT

A method is provided for performing nondestructive examination of a metal specimen using neutron activated positron annihilation wherein the positron emitter source is formed within the metal specimen. The method permits in situ nondestructive examination and has the advantage of being capable of performing bulk analysis to determine embrittlement, fatigue and dislocation within a metal specimen.

18 Claims, 2 Drawing Sheets

NONDESTRUCTIVE EXAMINATION USING NEUTRON ACTIVATED POSITRON ANNIHILATION

RELATED APPLICATION

This is a continuation-in-part of application Ser. No. 08/552,349 filed Nov. 2, 1995, now abandoned.

CONTRACTUAL ORIGIN OF THE INVENTION

The United States government has rights in this invention pursuant to Contract No. DE-AC-94ID13223 between the United States Department of Energy and Lockheed Martin Idaho Technologies Company.

BACKGROUND OF THE INVENTION

This invention relates to method and system for the nondestructive examination of the structural integrity of metals, and more specifically to a nondestructive examination to determine the extent of embrittlement, fatigue or dislocations throughout a metal specimen using neutron activated positron annihilation.

Fatigue in metal generally occurs in four stages: (1) early fatigue damage, (2) fatigue crack initiation, (3) fatigue crack growth, and (4) fracture. Most structural metals are polycrystalline and thus consist of a large number of individual ordered crystals or grains. The early fatigue damage generally consists of dislocations, dislocation loops and vacant lattice sites, which have accumulated into slip bands of dislocations within the grains. Some grains are oriented such that the planes of easy slip are in the direction of the maximum applied shear stress. Slip occurs in ductile metals within these individual grains by the dislocations moving along the crystalline planes.

Initially only a few bands are present in a few grains. As the fatigue cycling continues, more slip bands are observed in the grains with planes of easy slip in the direction of maximum applied shear stress, and more grains with slip bands are observed. Additional fatigue cycling creates more slip bands and also causes the slip bands to thicken. Most of the slip bands are on the component surface or on grain boundary surfaces and are not deep, but some are deep and are called "persistent slip bands".

Microscopic fatigue cracks generally grow from the persistent slip bands which intersect the component surface or the grain boundaries in the plane of the maximum shear stress range. As cycling continues, the microscopic fatigue cracks tend to coalesce and grow along planes of maximum tensile stresses. Crack initiation occurs when a microscopic crack grows to a detectable size or when several microscopic cracks join and form a detectable crack.

Early fatigue damage in either crystal defects or microscopic cracks is not detectable by standard NDE techniques such as x-ray diffraction, ultrasonic, eddy-current, magnetic techniques, and microstructural examinations. These techniques are capable of detecting a crack only after it reaches a significant size, that is, crack initiation stage.

Positron annihilation is a method that employs positrons from a radioactive source such as $^{22}$Na, $^{68}$Ge, or $^{58}$Co, to detect the presence of changes in the materials' microstructure caused by irradiation, cyclic loads or thermal exposure. A positron is a charged particle equal in mass to an electron and having a positive charge equal in magnitude to the negative charge of the electron.

Upon injection into metal, positrons rapidly lose most of their kinetic energy by collisions with ions and free electrons. An energetic positron injected into a solid is slowed down to thermal energies within 10 ps (1 ps=$10^{-12}$ s). Upon thermalization, the injected positron diffuses away from the point where it thermalized, until it finally annihilates with an electron. During this diffusion process, the positrons are repelled by positively charged nuclei and thus seek defects such as dislocations in the lattice sites, where the concentration of nuclei is lower. A thermalized positron has a typical mean velocity of approximate $10^5$ m/s. The balance between the diffusion rate (after thermalization) and the annihilation rate of thermalized positrons is such that on average each positron has time to diffuse just a few tens of a micrometer from its point of thermalization.

Typical lifetime and trial distance traveled by a thermalized positron before it annihilates with an electron are 200 ps and approximately 20 $\mu$m, respectively. The distance (~20 $\mu$m) traveled after thermalization encompasses about $10^5$ lattice sites, so there is a good chance that the position will encounter a defect and be trapped, even if the defects are present at quite small concentration (10 parts per million of defects ensures that on average there is one defect for every $10^5$ lattice sites).

Complete annihilation of both particles occurs when a positron encounters an electron and their mass is converted into pure energy in the form of two, or occasionally three, gamma rays. If the positron and the electron with which it annihilates were both at rest at the time of decay, the two gamma rays would be emitted in exactly opposite directions (180 degrees apart), in accordance with the principle of conservation of momentum. Each annihilation gamma ray would have an energy of 511 keV, the rest energy of an electron and of a positron. In fact however, nearly all the positrons are essentially at rest, but the electrons are not. The momentum of the electron determines the momentum of the annihilating pairs and causes the direction of the gamma rays to deviate from the nimial value of 180 degrees. Likewise, the energy of the annihilation gamma rays deviates slightly from 511 keV, depending on the momentum of the electron, because of the Doppler effect.

Although positron annihilation measurements have been successfully used in the laboratory to measure the fatigue of metal specimen materials, the technique has not been successfully utilized in field settings, such as nuclear power plants and in place structures. There are a number of reasons for this, including the fact that it is difficult to put a positron source and gamma ray detector inside a reactor pressure vessel or inside the primary coolant system piping. Also, postiron annihilation gamma rays are potentially subject to interference from radioactivity in or on the component to be examined.

Another reason that in-situ positron annihilation techniques have not been successful, in nuclear and nonnuclear environments, is that positron from $^{22}$Na or $^{68}$Ge sources only penetrate about 20 $\mu$m or 170 $\mu$m or less into steel. Therefore, conventional positron annihilation techniques are limited to near surface measurements and generally must be conducted under controlled laboratory conditions.

It is an aspect of the present invention to provide a nondestructive examination method having a neutron activated positron annihilation within a metal test specimen.

It is another aspect of the present invention to provide a nondestructive examination method utilizing data measured from neutron activated positron annihilation to determine embrittlement or fatigue within metal specimens.

It is still another aspect of the present invention to provide a positron annihilation method capable of nondestructively examining the internal (i.e., up to three and one half inches in steel) structure of a metal specimen.

SUMMARY OF THE INVENTION

To achieve the foregoing and other objects, the present invention provides a method for neutron activated positron annihilation nondestructive examination, the method comprising providing a metal specimen having a positron emitter source therein; activating the positron emitter source by neutron activation to generate gamma ray energy from positron annihilation within the metal specimen, the gamma ray energy then being emitted from the metal specimen; detecting the emitted gamma ray energy and establishing a width and high momentum structure of a detected 511 keV peak; and comparing the established width and high momentum structure of the 511 keV peak with a width and high momentum structure of a 511 keV gamma ray peak from positron annihilation of a known metal sample, said known metal sample being metallurgically similar in its composition to the metal specimen, and said known metal sample having known embrittlement or fatigue characteristicsm whereby the comparison facilitates characterization of embrittlement, fatigue or dislocations within the metal specimen.

BRIEF DESCRIPTION OF THE DRAWINGS

The present invention is illustrated in the accompanying drawings where.

DETAILED DESCRIPTION OF THE INVENTION

Figure 1:
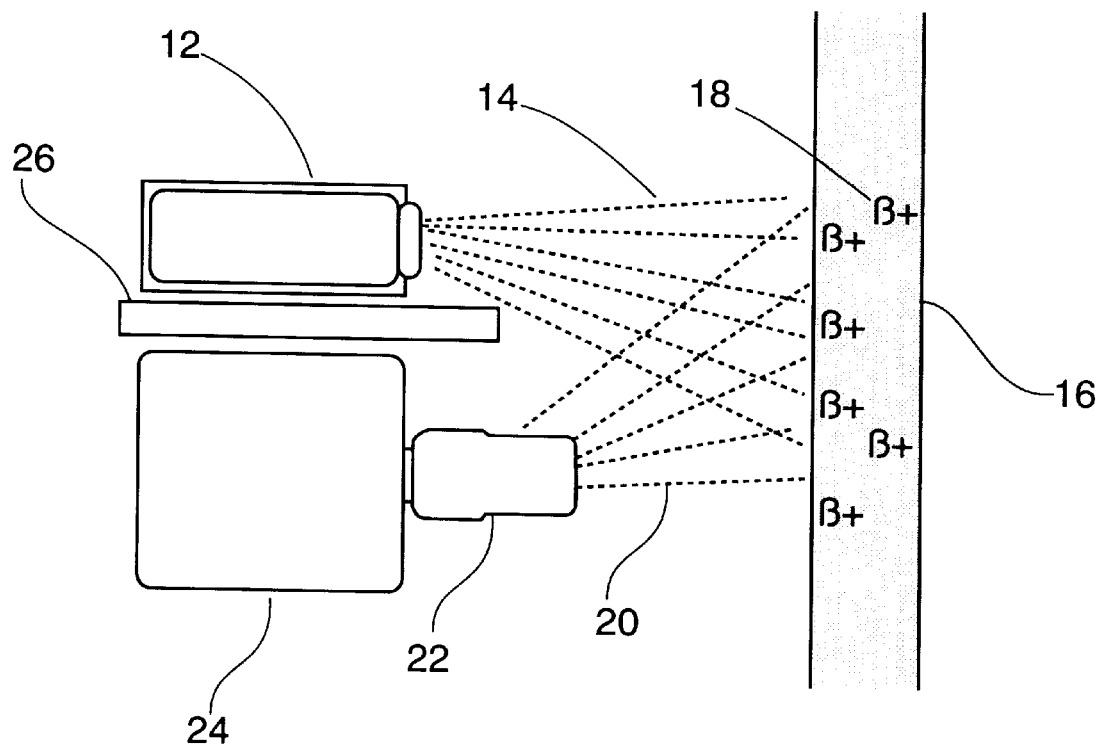
FIG. 1 is a schematic view of the method of the present invention illustrating the neutron activated positron annihilation within a metal test specimen.

Referring now to FIG. 1, a schematic view illustrating an embodiment of the present invention is shown. A neutron source 12 capable of providing neutrons shown. Preferably the neutrons provided from the neutron source 12 have an energy of up to 14 Mev. The neutron source can be a neutron generator or accelerator, such as a MF Physics A-320 probe detector by MF Physics Corporation, which is a variation on the basic A-320 design and is useful in applications where an extremely rugged, highly portable "probe" configured system is required. Alternatively, the neutron source of the present invention could be an isotopic source, such as $^{252}$Cf.

Neutrons from the neutron source are directed toward the metal test specimen 14. The metals capable of being tested using the present invention include: steel, aluminum, copper, and alloys thereof.

For example, neutron activation of the copper component of many such alloys, including Alcoa 6061/T6 aircraft aluminum which contains 0.25% copper, will produce a positron emitter disposed within the metal. The $^{63}$Cu (n, gamma) reaction produces $^{64}$Cu, a positron emitter having a 12 hour half life. Also, the $^{63}$Cu (n, 2n) reaction produces $^{62}$Cu, a positron emitter having a 9.7 minute half life. Neutron activation of copper in the alloy produces sufficient positrons for fatigue measurements of parts made from aluminum alloys containing at least one tenth of a percent of copper. Other elements found in some aluminum alloys include zinc, which may be also neutron activated to serve as a positron source. Positrons from these neutron activated alloy constituents have been found to be suitable for determining the strength loss from fatigue of components built from aluminum alloys and steel. Further, positrons from these neutron activated alloy constituents permit fatigue measurements to be made at far greater depths within aluminum alloy parts than are possible with external positron sources. Therefore a significant advantage of the present invention is the ability to perform bulk analysis of a metal specimen (e.g., at a depth of up to 3.5 inches in steel) using positron annihilation, rather than being limited to surface analysis (e.g. at a depth of approximately one tenth of an inch) as is achieved by conventional positron annihilation techniques.

Exposure of the aluminum alloy to a neutron flux of 1,000,000 neutrons per square centimeter per second for ten minutes has been observed to provide ample activation for measurement of fatigue and related defects in the aluminum alloy. This exposure will not cause measurable neutron embrittlement because measureable embrittlement does not occur until the alloy is subjected to a cumulative flux of $10^{15}$ neutrons per square centimeter. Therefore, use of the present invention on aircraft components can be performed in-situ and will not cause damage to the aircraft.

Another neutron activated positron source formed within a metal test specimen is $^{58}$Co, which is formed by in situ neutron capture from $^{59}$Co within the metal. It has been observed that there are sufficient $^{58}$Co produced positrons present during refueling shutdowns at nuclear power plants. The $^{58}$Co is produced during normal operation of a nuclear power plant and is deposited on the primary coolant system surfaces and fixed in the approximately 0.1 micron corrosion layer. The $^{58}$Co is also embedded throughout the reactor pressure vessel wall adjacent to the reactor.

Three characteristics of positrons and the radiation that they emit upon annihilation with electrons make the positron annihilation method of the present invention useful for detecting the presence and size of microscopic flaws in metals. First, the positive electrical charge cause positrons to be repelled by protons. This characteristic accounts for the positron's attraction to dislocations, vacant lattice sites, vacancy clusters, cavities and other open volumes (voids) in the metal, where the density of atomic nuclei is lower. Thus, a small increase in the number or size of the microscopic defects in a sample results in a large increase in the proportion of annihilation events occurring in the defects.

Second, annihilation radiation is sensitive to the momentum distribution of the electrons with which positron annihilate. Defects contain a higher ratio of free electrons to core electrons than perfect metal. This phenomenon can be explained by the tendency of free (conduction electron) to spill over into the defect more than core electrons. Core electrons have a much higher linear momentum than do free electrons. Thus, gamma rays from annihilation events involving free electrons are more likely to approximate the energy (511 keV) and direction (180 degrees) typical of gamma rays produced by events involving positrons and electrons at rest. These characteristics make it possible to detect the presence of defects from the energy spectrum of the gamma ray emissions and from the spectrum of angles of deviation from 180 degrees.

Third, because the density of electrons is lower in defects than in perfect metal, the mean lifetime of thermalized positrons trapped in defects is longer than those diffusing in perfect metal. Thus, measurement of positron lifetimes cans also be used to indicate the presence of defects in the metal.

As shown in FIG. 1, the gamma rays 20 resulting from the positron annihilation are emitted from the metal specimen 16 and collimated through a variable slit collimator 22 and detected by a high purity germanium detector 24. Preferably the detector 24 is shielded from the neutron source 12 by a neutron shield 26.

The collimator design required for these measurements is a variable slit collimator that allows the area of the metal being measured to be controlled so that the detector can be focused on specific areas such as a weld. The detector shielding configuration is shown schematically in FIG. 1. Interchangeable tungsten collimators with varying slit widths (nominally 1 inch long by either ⅛ inch and ⅝ inch wide) and a solid plug, are used with the shield/detector assembly for data acquisition. The detector/shield assembly is fixed in place at each measurement location with a specially designed strapping device that allows the detector to be attached to piping at any location. The collimator used was selected to achieve count rates that produced analyzer dead times less than 20%. The tungsten shield and the solid collimator plug provided at least two tenth-value layers for 1.3 MeV $^{60}$Co gamma rays. Background photopeak contributions from the solid collimator plug measurements are subtracted from those obtained with the open collimator.

The measurement system components are specifically chosen to minimize rate effects on the detector and maximize resolution. In addition, a pulser system is used on the analyzer to provide assurance that the measurements are being performed without rate-dependent effects on peak shape. The detector used was an ORTEC Gamma X detector with a Canberra Inspector multichannel analyzer system being used to perform measurements on samples where the positron source was place near the surface of the metal. The detector has a tungsten backshield to prevent a gamma-ray leakage into the detector. The detector was a 59% detector with a 1.95 keV Full Width and Half Max (FWHM) for $^{60}$Co at 1332 keV. Numerous detectors were evaluated to obtain one with the required stability in variable radiation fields and the necessary resolution for performing these measurements.

Figure 2:
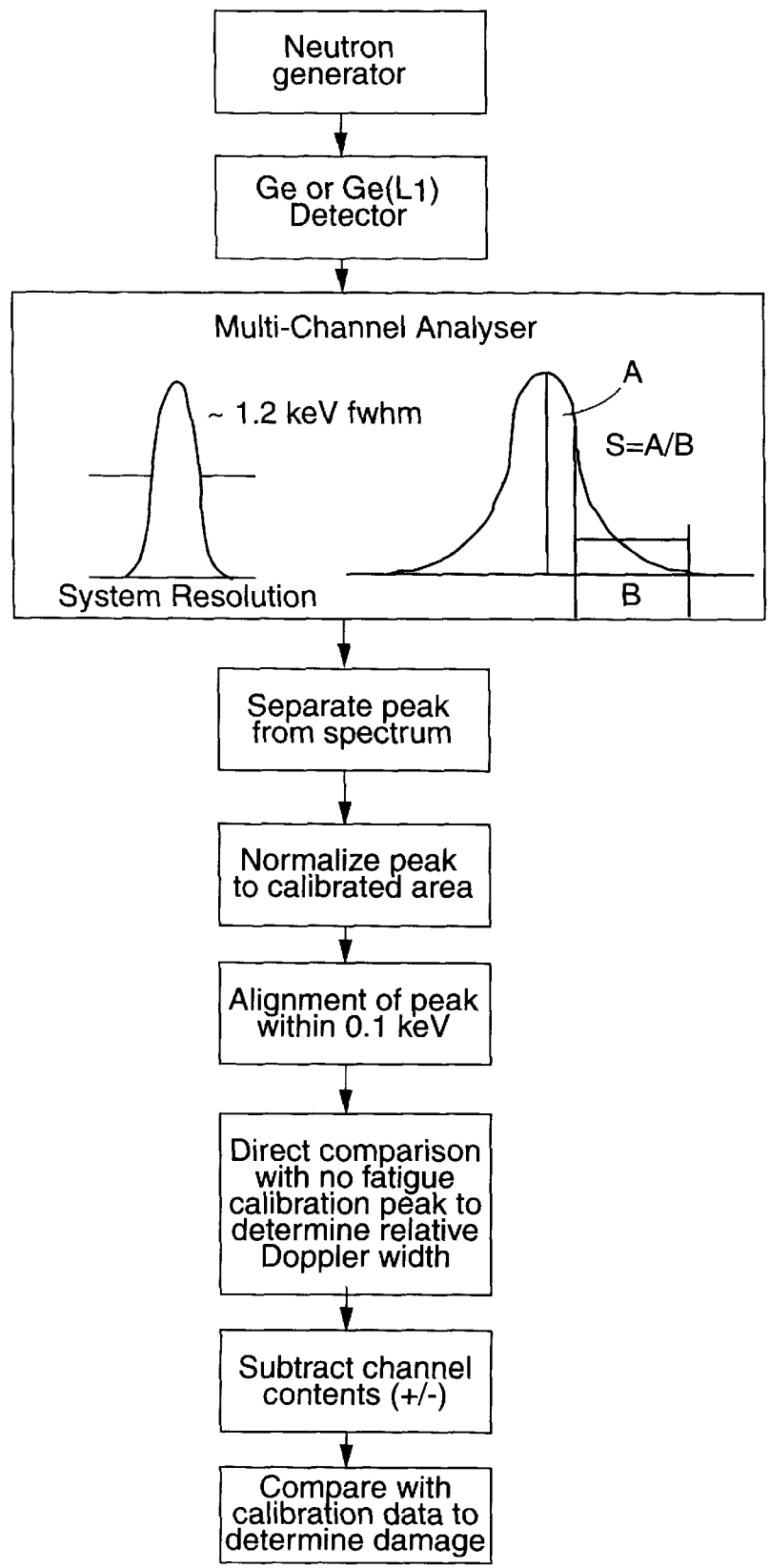
FIG. 2 is a schematic flow chart depicting the method of the present invention.

An example of an analysis system used in the present invention is a Canberra Inspector that had been specially modified so that pulse injection with subsequent removal to confirm that the spectrum was obtained in a stable environment and that gain shifts did not occur during data acquisition. The system had the following features: (a) pulser calibration can remain accurate for months, (b) automatic monitoring of the channel positions, shape of the pulser peaks for gain and zero shifts, extraneous noise, and (c) automatic correction for dead time and random summing. This system was temperature stable over the range 0° to 100° C. with a drift of less than 0.5 keV. Variation in the stability as a function of count rate is less than 3% over the range up to 135,000 counts per second. Referring now to FIG. 2, the method of the present invention is illustrated in schematic form. The data are in the form of gamma ray counts versus gamma ray energy. A parameter S, called a line-shape parameter, is used to measure the gamma spectrum width. The line-shape parameter is equal to the ratio of the number of counts in Region A to the total number of counts under the curve. The value of S increase as the number of defects within the specimen increases.

The section of the gamma ray spectrum within 10 keV on each side of the 511 keV positron annihilation peak is extracted from the spectrum for analysis. This is referred to in this application as the "width" of the 511 keV peak. This section of the spectrum is integrated to determine the total number of counts in the spectrum and then is normalized to a predetermined integral quantity (nominally 10M counts). The centroid of the peak is then mathematically adjusted to a previously determined energy within 0.1 keV of the 511 keV peak.

The channel contents of the channels above the adjusted centroid channel are then extracted from the spectrum section and the FWHM is calculated for the portion of the peak above the 511 keV energy. This is referred to in this application as the "high momentum structure" of the 511 keV peak. This provides an initial assessment of the peak shape and Doppler broadening of the peak when compared with standard peak shapes as defined by standard FWHM for the detector being used.

The section of the spectrum above 511 keV channel is then compared on a channel by channel basis with reference spectra with know fatigue or embrittle levels. Then two spectral sections are identified that most closely bound the measured spectrum, interpolation is performed on the channel contents to determine the exact fatigue of embrittlement level by determining the average difference between the two fatigue levels and calculating the average fatigue based on interpolation of the values.

A statistical uncertainty is then calculated by summing the differences in the channel contents between the measure spectrum section and the reference spectrum that is closest to the measured spectrum. The average uncertainty in the difference between the two spectral sections is calculated. This is necessary because the actual shape of the peak may vary based on temperature and other effects that may affect the shape of the peak. These uncertainties are reflected in the uncertainty associated with the fatigue measurement being performed. The fatigue or embrittlement level with an uncertainty associated that reflects how closely the measured spectrum reflects that section of the reference spectrum can then be reported and/or displayed by computer.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical application and enable others skilled in the art to utilize the invention in various embodiments and with various modifications as are suited to the particular use contemplated. It is intended that the scope of the invention be defined by the claims appended hereto.

We claim:

1. A method for the nondestructive determination of embrittlement, fatigue or dislocations within a metal, comprising:

(a) providing a metal specimen having a positron emitter source therein;

(b) activating the positron emitter source by neutron activation to generate gamma ray energy from positron annihilation within the metal specimen, the gamma rays then being emitted from the metal specimen;

(c) detecting the emitted gamma rays and establishing a width and high momentum structure of a detected 511 keV peak;

(d) comparing the established width and high momentum structure of the 511 keV peak with a width and high momentum structure of a 511 keV gamma ray peak from positron annihilation of a known metal sample, said known metal sample being metallurgically similar in its composition to the metal specimen, and said known metal sample having known embrittlement or fatigue characteristics, whereby said comparison facilitates characterization of embrittlement, fatigue or dislocations within the metal specimen.

2. The method of claim 1 wherein the positron emitter source within the metal specimen is a copper isotope.

3. The method of claim 1 wherein the positron emitter source within the metal specimen is a cobalt isotope.

4. The method of claim 1 wherein the positron emitter source within the metal specimen is a zinc isotope.

5. The method of claim 1 wherein the metal specimen is steel.

6. The method of claim 1 wherein the metal specimen is aluminum or alloys thereof.

7. The method of claim 1 wherein the neutron activation is by use of a neutron generator.

8. The method of claim 1 wherein the neutron activation is by use of an isotopic neutron source.

9. The method of claim 8 wherein the isotopic neutron source is $^{252}$Cf.

10. A method for the nondestructive determination of embrittlement, fatigue and dislocations within a metal, comprising:

(a) providing a metal specimen having a positron emitter source therein;

(b) activating the positron emitter source by neutron activation to generate gamma ray energy from positron annihilation within the metal specimen, the gamma ray energy then being emitted from the metal specimen;

(c) detecting the emitted gamma ray energy (d) establishing a 511 keV peak ±10 keV spectrum section;

(e) adjusting a centroid of the established peak to a previously determined energy within 0.1 keV of the 511 keV peak;

(f) extracting channel contents of channels above the adjusted centroid;

(g) calculating a full width at half max for a portion of the adjusted centroid above 511 keV; and (h) comparing on a channel-by-channel basis the established spectrum section above 511 keV with a reference spectra having known fatigue or embrittlement levels to determine the embrittlement, fatigue or dislocations characteristics of the metal specimen.

11. The method of claim 10 wherein the positron emitter source within the metal specimen is a copper isotope.

12. The method of claim 10 wherein the positron emitter source within the metal specimen is a cobalt isotope.

13. The method of claim 10 wherein the positron emitter source within the metal specimen is a zinc isotope.

14. The method of claim 10 wherein the metal specimen is steel.

15. The method of claim 10 wherein the metal specimen is aluminum or alloys thereof.

16. The method of claim 10 wherein the neutron activation is by use of a neutron generator.

17. The method of claim 10 wherein the neutron activation is by use of an isotopic neutron source.

18. The method of claim 17 wherein the isotopic neutron source is $^{252}$Cf.

* * * * *